United States Patent
Weisbeck et al.

(12) United States Patent (10) Patent No.: US 6,995,113 B1
(45) Date of Patent: Feb. 7, 2006

(54) CATALYSTS WHICH ARE BASED ON ORGANIC-INORGANIC HYBRID MATERIALS CONTAINING NOBLE METALS AND TITANIUM AND WHICH ARE USED FOR SELECTIVELY OXIDIZING HYDROCARBONS

(75) Inventors: Markus Weisbeck, Köln (DE); Gerhard Wegener, Mettmann (DE); Georg Wiessmeier, Bergisch Gladbach (DE); Peter Vogtel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 366 days.

(21) Appl. No.: 10/149,056

(22) PCT Filed: Nov. 27, 2000

(86) PCT No.: PCT/EP00/11781

§ 371 (c)(1),
(2), (4) Date: Jun. 6, 2002

(87) PCT Pub. No.: WO01/41921

PCT Pub. Date: Jun. 14, 2001

(30) Foreign Application Priority Data

Dec. 9, 1999 (DE) .................................. 199 59 525

(51) Int. Cl.
*B01J 21/08* (2006.01)
*B01J 21/12* (2006.01)
*B01J 21/14* (2006.01)
*B01J 23/00* (2006.01)

(52) U.S. Cl. .................. 502/243; 502/236; 502/239; 502/244; 502/347; 502/350

(58) Field of Classification Search ................ 502/239, 502/243, 236, 344, 347, 350
See application file for complete search history.

(56) References Cited

U.S. PATENT DOCUMENTS

| | | | | |
|---|---|---|---|---|
| 4,273,902 A | * | 6/1981 | Tomioka et al. | 525/478 |
| 5,017,540 A | * | 5/1991 | Sandoval et al. | 502/158 |
| 5,326,738 A | * | 7/1994 | Sandoval et al. | 502/401 |
| 5,492,958 A | * | 2/1996 | Haluska et al. | 524/439 |
| 5,534,609 A | * | 7/1996 | Lewis et al. | 528/15 |
| 5,623,090 A | | 4/1997 | Haruta et al. | 568/360 |
| 5,677,410 A | | 10/1997 | Mager et al. | 528/15 |
| 5,747,623 A | * | 5/1998 | Matsuo et al. | 528/14 |
| 5,912,377 A | * | 6/1999 | Hall et al. | 556/415 |
| 5,932,750 A | | 8/1999 | Hayashi et al. | 549/523 |
| 6,013,711 A | * | 1/2000 | Lewis et al. | 524/265 |
| 6,034,028 A | | 3/2000 | Hayashi et al. | 502/243 |
| 6,316,057 B1 | * | 11/2001 | Hirayama et al. | 427/400 |

FOREIGN PATENT DOCUMENTS

EP   10 05 907   6/2000

(Continued)

OTHER PUBLICATIONS

Catal. Rev.-Sci. Eng., 23(1&2), month unavailable 1981, pp. 127-149, "On the Mechanism of Ethylene-Epoxidation," W.M.H. Sachtler, C. Backx and R.A. Van Santen.

*Primary Examiner*—Cam N. Nguyen
(74) *Attorney, Agent, or Firm*—Joseph C. Gil; John E. Mrozinski, Jr.

(57) ABSTRACT

The present invention relates to noble metal-containing catalysts which are composed of at least one organic/inorganic hybrid material which is composed of at least one titanium component and at least one Si—H group. The catalysts of the present invention have increased activity compared to known catalysts.

12 Claims, 1 Drawing Sheet

FOREIGN PATENT DOCUMENTS

| | | |
|---|---|---|
| WO | 98/00413 | 1/1998 |
| WO | 99/26936 | 6/1999 |
| WO | 99/43431 | 9/1999 |
| WO | 00/64581 | 2/2000 |
| WO | 00/64582 | 11/2000 |
| WO | 00/74841 | 12/2000 |

* cited by examiner

Figure 1

CATALYSTS WHICH ARE BASED ON ORGANIC-INORGANIC HYBRID MATERIALS CONTAINING NOBLE METALS AND TITANIUM AND WHICH ARE USED FOR SELECTIVELY OXIDIZING HYDROCARBONS

TECHNICAL FIELD OF THE INVENTION

The present invention provides compositions which contain gold and/or silver particles and titanium-containing organic/inorganic hybrid materials, wherein these hybrid materials contain Si—H groups, a process for their preparation and their use as catalysts for the selective oxidation of hydrocarbons. The catalytically active compositions exhibit high selectivities and productivities and very long catalyst operational lifetimes without deactivating.

BACKGROUND OF THE INVENTION

The direct oxidation of ethene to ethene oxide by molecular oxygen is well known and is used commercially for the production of ethene oxide in the gas phase. The typical catalyst for this application contains metallic or ionic silver, possibly modified with various promoters and activators. Most of these catalysts contain a porous, inert catalyst support with a low surface area such as e.g. alpha-aluminium oxide, on which the silver and promoters have been applied. A review of the direct oxidation of ethene in the presence of supported silver catalysts has been provided by Sachtler et al. in Catalysis Reviews: Science and Engineering, 23 (1&2), 127–149 (1981).

U.S. Pat. No. 5,623,090 describes a gas phase direct oxidation of propene to give propene oxide with relatively small propene conversions (0.5–1% propene conversion, with respect to a 10% propene feed concentration), but with propene oxide selectivities of >90%, using oxygen as the oxidising agent. This is a gold/titanium dioxide catalysed gas phase oxidation with molecular oxygen in the presence of hydrogen at temperatures of 40–70° C. The catalyst used is a commercially available crystalline titanium dioxide, mainly in the anatase modification (P 25, Degussa; 70% anatase and 30% rutile), which is coated with nanoscale gold particles using a deposition-precipitation method. Apart from the relatively low propene conversions, this process has the large disadvantage that the disclosed catalysts deactivate strongly with time. Typical half-life values at atmospheric pressure and 50° C. are 30–150 minutes. Increasing the temperature and/or the pressure to increase the conversion shortens the half-life even more.

Furthermore, purely inorganic catalysts, in which gold particles from suitable soluble gold compounds are applied by deposition-precipitation to a support consisting of dispersed titanium oxide centres on a purely inorganic silicon matrix, are also known (WO-98/00415; WO-98/00414; EP-A1-0 827 779). WO-98/00415 and WO-98/00414 stress that all the titanium oxide centres are present in amorphous form, i.e. that, differently from U.S. Pat. No. 5,623,090, no crystalline $TiO_2$ phase is present. All these catalysts, which are materials obtained by impregnating the purely inorganic silicon dioxide surface with titanium precursors in solution and then coating with gold by deposition-precipitation and subsequent calcination in an atmosphere of air, exhibit relatively low propene conversions and deactivate rapidly (typical half-lives are 10–50 hours) and cannot therefore be used in industrial-scale plant.

WO-98/00413 discloses catalysts in which gold particles are applied to purely inorganic, microporous, crystalline lattice silicates with defined pore structures (e.g. TS-1, TS-2, Ti-zeolites such as Ti-beta, Ti-ZSM-48 or titanium-containing, mesoporous molecular sieves such as e.g. Ti-MCM-41 or Ti-HMS). Although all these purely inorganic gold/silicalite or gold/zeolite catalysts exhibit good selectivities during partial oxidation, the conversions of hydrocarbons and in particular the catalyst operational lifetimes are completely inadequate for application in the chemical industry.

The methods described for catalyst preparation are at best unsatisfactory with regard to catalyst activity and lifetime. Enormous reactors are required for industrial processes which operate with not very active catalysts. Low catalyst lifetimes incur production downtime during the regeneration phase or demand a redundant, cost-intensive, production path. Thus there is a need for the development of new catalysts which can achieve excellent selectivities and high activities with industrially relevant lifetimes.

The use of organic/inorganic hybrid materials as lacquer components is known (e.g. EP-A1-743 313). The combination with noble metals and titanium or their use as a catalyst is not known.

Previously-dated application DE 199 18 431.3 describes a supported composition containing gold and/or silver particles, titanium oxide and a silicon-containing support which is characterised in that the composition carries groups chosen from siliconalkyl, siliconaryl, fluorine-containing alkyl or fluorine-containing aryl groups at the surface, as the result of a subsequent modification step, and also their use as catalysts for the direct oxidation of hydrocarbons. Organic/inorganic hybrid materials are not disclosed as supports.

Application WO 99/43431 describes catalysts in which gold particles from suitable soluble gold compounds are applied by deposition-precipitation to a support which consists of dispersed titanium oxide centres on a purely inorganic silicon matrix (due to solvent impregnation with titanium precursors) and is subsequently surface-modified with a silylating agent. Organic/inorganic hybrid materials are not disclosed as supports.

Previously dated application DE 199 20 753.4 describes a supported composition containing gold and/or silver particles and an amorphous titanium/silicon mixed oxide characterised in that the titanium/silicon mixed oxide is prepared by a sol-gel process. No compositions which contain Si—H groups are disclosed.

Previously dated application DE 199 25 926.7 describes noble metal-containing Ti/Si mixed oxides as catalysts with organic/inorganic hybrid materials based on carbosiloxanes for the direct oxidation of hydrocarbons, and the preparation thereof by a sol-gel process. However, no compositions which contain Si—H groups are disclosed.

The present invention provides new catalysts for industrial processes which exhibit high activities without deactivating and at the same time possess excellent selectivities.

SUMMARY OF THE INVENTION

The invention also develops a process for preparing these catalysts.

The invention also provides a technologically simple gas phase process for the selective oxidation of hydrocarbons with a gaseous oxidising agent on these catalysts which, with high activities, very high selectivities and industrially relevant catalyst lifetimes, leads to high yields and low costs.

DETAILED DESCRIPTION OF THE INVENTION

The invention also provides an alternative catalyst for the direct oxidation of hydrocarbons.

The invention also eliminates, at least to some extent, the disadvantages of known catalysts.

These objects are achieved by a composition which contains gold and/or silver particles on a titanium-containing, organic/inorganic hybrid material, characterised in that the composition contains Si—H groups.

Organic/inorganic hybrid materials in the context of the invention are organically modified glasses which are preferably produced in sol-gel processes via hydrolysis and condensation reactions of mostly low molecular weight compounds and contain terminal and/or bridging organic groups within the network.

Organic/inorganic hybrid materials with large specific surface areas are preferred. The specific surface area should advantageously be more than 1 $m^2/g$, preferably in the range 10–700 $m^2/g$.

Furthermore, organic/inorganic hybrid materials with modified surfaces are preferred. Modified surfaces in the context of the invention means that the proportion of surface silanol groups has been reduced by covalent or coordinative bonding of groups chosen from siliconalkyl, siliconaryl, fluorine-containing alkyl and/or fluorine-containing aryl groups.

The composition according to the invention contains gold and/or silver on the organic/inorganic hybrid material as a catalytically active support material. In the active catalysts, gold and/or silver are mainly present as the elemental particles (analysis by X-ray absorption spectroscopy). Small proportions of the gold and/or silver may also be present in a higher oxidation state. Judging from TEM images, the greatest proportion of the gold and/or silver is present on the external and internal surfaces of the support material. The gold and/or silver forms clusters on the nanometre scale. Gold particles preferably have a diameter in the range 0.3 to 50 nm, preferably 0.9 to 15 nm and in particular 0.9 to 10 nm. Silver particles preferably have a diameter in the range 0.5 to 100 nm, preferably 0.5 to 40 nm and in particular 0.5 to 20 nm.

The gold concentration should be in the range 0.001 to 4 wt. %, preferably 0.001 to 2 wt. % and in particular 0.005 to 1.5 wt. % of gold.

The silver concentration should be in the range 0.005 to 20 wt. %, preferably 0.01 to 15 wt. % and in particular 0.02 to 10 wt. % of silver.

For economic reasons, the concentration of noble metal is the minimum amount required to provide the highest catalytic activity.

Production of the noble metal particles on the hybrid materials is not restricted to one method. A few example processes for the generation of gold and/or silver particles may be mentioned here, such as deposition-precipitation as described in EP-B-0 709 360 on p. 3, line 38 et seq., impregnation in solution, incipient wetness, colloid processes, sputtering, CVD and PVD. It is also possible to integrate precursor compounds of the noble metals directly in the sol-gel process. After drying and conditioning the noble metal-containing gels, nanoscale gold and/or silver particles are also obtained. Incipient wetness is understood to mean the addition of a solution containing soluble gold and/or silver compounds to the support material, wherein the volume of the solution on the support is less than or equal to the pore volume of the support. Thus, the support remains dry on a macroscopic scale. Any solvent in which the noble metal precursors are soluble may be used as the solvent for incipient wetness, such as water, alcohols, ethers, ketones, esters, acetals, halogenated hydrocarbons, etc.

Nanoscale gold and/or silver particles are preferably produced by the methods of incipient wetness and solvent impregnation.

Surprisingly, the generation of nanoscale gold particles from soluble gold compounds such as tetrachloroauric acid, e.g. by the incipient wetness method, can also take place in the presence of oligomeric or polymeric auxiliary substances such as polyvinylpyrrolidone, polyvinyl alcohol, polypropylene glycol, polyacrylic acid, etc. or in the presence of complex-forming components such as cyanides, acetylacetone, ethylacetoacetate, etc. Complex-forming additives such as cyanides, e.g. alkali metal or alkaline earth metal cyanides, are preferably used.

Compositions according to the invention may advantageously be further activated, before and/or after being coated with noble metal, by thermal treatment at 100–1200° C. in a variety of atmospheres such as air, nitrogen, hydrogen, carbon monoxide or carbon dioxide. Thermal activation at 150–500° C. in oxygen or oxygen-containing gases such as air or oxygen/hydrogen or oxygen/rare gas mixtures or combinations thereof or at 150–1000° C. under inert gases such as nitrogen and/or hydrogen and/or rare gases or combinations thereof is preferred. The presence of carbon monoxide, carbon dioxide and small amounts of water is often advantageous. Activation of compositions according to the invention under inert gases in the temperature range 200–600° C. is particularly preferred. However, it may also be advantageous to condition support materials according to the invention at temperatures in the range 200–1000° C., to coat these with noble metal and then to repeat the conditioning process at 200–600° C. Depending on the activation temperature chosen, chemical processes alter the structure of compositions according to the invention. Thus, after thermal treatment, the compositions may contain e.g. siliconoxycarbide units. Thermally activated (conditioned) compositions according to the invention frequently exhibit a significantly higher catalytic activity and extended lifetime when compared with known catalysts.

Organic/inorganic hybrid materials in the context of the invention contain between 0.1 and 20 mol. % of titanium, preferably between 0.8 and 10 mol. %, in particular between 1.0 and 8 mol. %, with respect to the silicon oxide. The titanium is present in oxidic form and is preferably chemically incorporated or bonded homogeneously within the organic/inorganic hybrid materials via Si—O—Ti bonds. Active catalysts of this type have only very few Ti—O—Ti domains.

Without wishing to be held to this, we assume that the titanium in active catalysts is bonded to silicon via heterosiloxane bonds.

Apart from titanium, compositions according to the invention may contain further foreign oxides, so-called promoters, from group 5 in the Periodic System according to IUPAC (1985), such as vanadium, niobium and tantalum, preferably tantalum, from group 3, preferably yttrium, from group 4, preferably zirconium, from group 8, preferably Fe, from group 15, preferably antimony, from group 13, preferably aluminium, boron, thallium and metals from group 14, preferably germanium.

These promoters are advantageously distributed largely homogeneously, i.e. with relatively little domain formation. The incorporated promoters "M" are generally dispersed within the organic/inorganic hybrid materials. The chemical composition of these materials can vary over a wide range. The proportion of promoter element is in the range 0–10 mol. %, preferably 0–4 mol. %, with respect to silicon oxide. Obviously, several different promoters may also be used. The promoters are preferably used in the form of promoter precursor compounds which are soluble in the particular solvent, such as promoter salts and/or promoter-organic compounds and/or promoter-organic-inorganic compounds.

These promoters may both increase the catalytic activity of the composition and increase the operational lifetime of the composition during catalytic oxidation reactions of hydrocarbons.

Compositions according to the invention which contain gold and/or silver particles and Ti-containing, organic/inorganic hybrid materials with Si—H groups may be described approximately by the following empirical general formula (I) in the dry state (the groups formed at the surface after modification and optionally incompletely reacted groups are not taken into account here):

$$SiO_x*Org*H*TiO_y*MO_z*E \qquad (I)$$

$SiO_x$ represents silicon oxide, Org in the formula represents the non-hydrolysable organic constituents formed from the organic/inorganic precursors, preferably in a sol-gel process, gives the molar proportion of "element"-H groups in the network, wherein "element" differs from carbon, M is a promoter, preferably Ta, Fe, Sb, V, Nb, Zr, Al, B, Tl, Y, Ge or combinations thereof, represents gold and/or silver (noble metal) and x, y and z stand for the effective number of oxygen atoms required to saturate the valencies of the organic/inorganic or purely inorganic elements Si, Ti and M.

The composition (I) given above can vary over a wide range.

The proportion of Org, as mole percentage with respect to silicon oxide, may be between 0.01 and 200%. It is preferably between 10 and 2000%, in particular between 30 and 100%. The molar proportion of Si—H units with respect to silicon oxide may vary between 0.01 and 100 mol. %. This proportion is preferably between 0.05 and 80%, in particular between 0.1 and 50 mol. %. The proportion of titanium oxide with respect to silicon oxide is between 0.1 and 10 mol. %, preferably between 0.5 and 8.0%, in particular between 0.5 and 7.0%. The proportion of $MO_z$ with respect to silicon oxide is between 0 and 12 mol. %. The proportion of with respect to the gold- and/or silver-free composition is between 0.001 and 15 wt. %. In the case of gold this proportion is preferably between 0.001 and 2 wt. % and for silver it is preferably between 0.01 and 15 wt. %.

The objects indicated above are also achieved by a process for preparing compositions according to the invention which contain gold and/or silver particles and Ti-containing, organic/inorganic hybrid materials with Si—H groups.

The Ti-containing organic/inorganic hybrid materials with silane hydrogen units are prepared by a sol-gel process. This takes place, for example, by mixing suitable, mostly low molecular weight, compounds in a solvent, wherein the hydrolysis and condensation reaction is initiated by adding water and optionally catalysts (e.g. acids, bases and/or organometallic compounds and/or electrolytes). Basically, performing this type of sol-gel process is known to a person skilled in the art.

Suitable precursor compounds for silicon, titanium and promoter centres are advantageously corresponding, mostly low molecular weight, organic/inorganic mixed compounds or a combination of corresponding inorganic and organic/inorganic mixed compounds which are suitable for the sol-gel process. Low molecular weight in the context of the invention means monomers or oligomers. Polymeric precursor compounds of silicon, titanium and promoters are also suitable if they are sufficiently soluble.

The sol-gel process is based on the polycondensation of the hydrolysed, colloidally dissolved metal component mixture (sol) with the production of a network (gel). To explain this, the following schematic representation, using the example of the hydrolysis and condensation of tetraalkoxysilanes to give a purely inorganic polysiloxane network, is used:

Hydrolysis is achieved by initially introducing the hydrolysable Si and/or Ti precursor in a suitable solvent and then mixing with water and optionally homogenising the mixture with dissolution aid. Since the hydrolysis of silicon precursor compounds is slow under normal conditions, catalysts are required in order to make it proceed rapidly and completely (J. Livage et al., Chemistry of Advanced Materials: An Overview; eds: L. V. Interrante et al., VCH, New York, 1998, p. 389–448). The silanols being produced condense with the formation of siloxane compounds. Dissolved polysiloxane networks are then produced. Branching and cross-linking continue until the polymer is so large that the transition to a gel takes place. Initially, the gel consists of a solid polymeric network which is permeated with solvent. During the subsequent drying stage, the network shrinks with loss of the solvent, wherein a xerogel consisting of polysiloxane is produced. If the gel is dried under supercritical conditions, the resulting product is then called an aerogel (A. Baiker et al., Catal. Rev. Sci. Eng. 1995, 37, 515–556).

Preferred solvents for the sol-gel process are alcohols such as tert.-butanol, isopropanol, butanol, ethanol, methanol or ketones such as acetone and ethers such as e.g. THF or tert.-butyl methyl ether.

Suitable starting materials are all the soluble silicon and titanium compounds of the general formula (II) which are known to a person skilled in the art, which may be used as starting materials for the corresponding oxides or hydroxides, $$[R_xM'(OR')_{4-x}] \qquad (II),$$

wherein
M' is chosen from silicon and titanium,
R and R' are identical or different and are chosen, independently, from the groups $C_1$–$C_{12}$-alkyl and $C_6$–$C_{12}$ aryl, wherein x=0, 1, 2, 3 and R' may also be H.

In the case of organically modified silanes, one or more hydrolysable groups have been replaced by terminal and/or bridging saturated (e.g. $CH_3$, $C_2H_5$, $C_3H_7$, ... ) group(s) or unsaturated (e.g. $C_2H_3$, $C_6H_5$) group(s). Polyfunctional organosilanes, e.g. silanols and alkoxides, may also be used. Silanes, organically modified or not, may also be reacted in the presence of dihydric or polyhydric alcohols such as 1,4-butanediol, to give organically modified polysiloxanes. Bridging groups (alkylene groups) in the context of the invention are bridging structures such as chain-shaped, star-shaped (branched), cage-shaped or ring-shaped structural elements.

The modified silanes used here clearly differ from the inorganic network producers which are conventionally used, such as alkoxysilanes [Si(OR)$_4$] with four hydrolysable groups which are used, e.g. to prepare crystalline lattice structures with defined pore structures (WO-98/00413; TS 1, TS 2, Ti-MCM 41 and 48).

In contrast to the catalysts according to the invention, a common feature of all the previously disclosed catalysts is that the gold particles have been applied to purely inorganic support materials, i.e. that the solid lattice consists of purely inorganic silicon-oxygen and titanium-oxygen units.

Alkyl is understood to mean all the terminal and/or bridging linear or branched alkyl groups with 1 to 20 carbon atoms known to a person skilled in the art, such as methyl, ethyl, n-propyl, i-propyl, n-butyl, i-butyl, t-butyl, n-pentyl, i-pentyl, neo-pentyl, hexyl and other homologues, which for their part may again be substituted. Suitable substituents are halogen, nitro, or also alkyl, hydroxide or alkoxy, as well as cycloalkyl or aryl, such as benzoyl, trimethylphenyl, ethylphenyl, chloromethyl, chloroethyl and nitromethyl. Nonpolar substituents such as methyl, ethyl, n-propyl, i-propyl, n-butyl, i-butyl, t-butyl and benzoyl are preferably used. High molecular weight and/or oligomeric organic/inorganic silicon and titanium precursors are also suitable, such as gamma-glycidoxypropyltrimethoxysilane, 3,4-epoxycyclohexyl-ethyl-trimethoxysilane, 1-(triethoxysilyl)-2-(diethoxymethylsilyl)ethane, tris-(gamma-trimethoxypropyl) silicon isocyanurate, peralkylated cyclosiloxanes such as hexamethylcyclotrisiloxane, octamethyltetrasiloxane or decamethylpentasiloxane. Polyalkyl(aryl)siloxanes such as polydimethylsiloxane are also suitable.

Aryl is understood to be all mononuclear or polynuclear aryl groups with 6 to 12 carbon atoms which are known to a person skilled in the art, such as phenyl, naphthyl or fluorenyl, which for their part may again be substituted. Suitable substituents here are halogen, nitro or also alkyl or alkoxy, as well as cycloalkyl or aryl, such as bromophenyl, chlorophenyl, toluyl and nitrophenyl. Phenyl, fluorenyl, bromophenyl, chlorophenyl, toluyl and nitrophenyl are preferred.

Examples are the corresponding alkoxides, soluble salts and organosilicon or organotitanium compounds.

Although any salts, such as halides, nitrates and hydroxides, may be used, the alkoxides, e.g. n-butoxide, tert.-butoxide, isopropoxide, n-propoxide, ethoxide or methoxide, of these elements are preferred.

Titanium derivatives such as tetraalkoxy titanates, with alkyl groups with 1 to 15 carbon atoms such as iso-butyl, tert.-butyl, n-butyl, i-propyl, propyl, ethyl, etc., or other organic titanium species such as titanyl acetylacetonate, dicyclopentadienyltitanium dihalides, titanium halodialkoxides, titanium halotrialkoxides, are preferably used. In the case of halogen substituents, chlorine is preferred. Mixed alkoxides of titanium with other elements, such as e.g. titanium triisopropoxide tri-n-butyl tin oxide, may also be used. The titanium precursor compounds may also be used in the presence of complex-forming components such as e.g. acetylacetone or ethylacetoacetate.

The organic/inorganic silicon and titanium precursor compounds may also be used in combination with inorganic network-producers such as tetraethoxysilane (Si(OC$_2$H$_5$)$_4$) and tetramethoxysilane (Si(OCH$_3$)$_4$) or homologues of these. Instead of monomeric alkoxides, their condensation products may also be used. For example, Si(OC$_2$H$_5$)$_4$ condensates are commercially available. Furthermore, oligomeric or polymeric systems such as poly(diethoxysiloxane) may also be used.

The silicon and titanium compounds mentioned are advantageously used in combination with silanes of the general formula (IIIa) or (IIIb), (IIIa)

(IIIb)

wherein
R and R' are identical or different and, independently, are chosen from the group $C_1$–$C_{12}$-alkyl, $C_6$–$C_{12}$-aryl, where x=0, 1, 2, 3 and y=1, 2, 3 and R' and may also be H.

The Si—H containing silanes may also be generated in situ from e.g. halosilanes in the presence of reducing agents such as e.g. magnesium hydride.

Compounds of the general formulae (IIIa) and (IIIb) may be replaced entirely or partly by other silicon precursor compounds which contain some Si—H units such as e.g. 1,1,3,3-tetramethyldisiloxane, 1,3,5,7-tetramethylcyclotetrasiloxane, tri-n-hexylsilane, triphenylsilane.

Examples of silanes are monoalkoxysilanes ($C_1$–$C_{12}$), dialkoxysilanes ($C_1$–$C_{12}$), trialkoxysilanes ($C_1$–$C_{12}$), dialkoxy-monohalosilanes ($C_1$–$C_{12}$), monoalkoxydihalosilanes ($C_1$–$C_{12}$), methylhydrocyclosiloxane, trihalosilane, dihalosilane, monohalosilane.

$C_1$–$C_{12}$ trialkoxysilanes are preferred, such as trimethoxysilane, triethoxysilane, triisopropoxysilane, tripropoxysilane and tributoxysilane.

With respect to silicon oxide, the molar concentration of silane hydrogen in the cocondensate (product of the sol-gel process) is preferably in the range 0.01–100 mol. %, in particular 0.1–50 mol. %.

Surprisingly, we found that the organic/inorganic hybrid materials with a proportion of silane hydrogens are particularly suitable for the application of metals such as gold and silver with a high degree of dispersion and improved noble metal/support interaction on the external and internal surfaces. Nanoscale metal particles are generated. In contrast, it is possible in only an unselective manner to synthesise nanoscale metal particles with a very narrow particle size distribution on purely inorganic silica or $SiO_2/TiO_2$ mixed oxide surfaces (analogous to WO-98/00415, WO-98/00414, WO-98/00413, EP-A1-0 827 779), i.e. without any organic modification and in particular without a proportion of silane hydrogens.

Surprisingly, we have found that compositions according to the invention, in comparison to all hitherto known catalyst systems for the catalytic oxidation of unsaturated and saturated hydrocarbons, frequently exhibit catalytic activities and catalyst lifetimes which are several orders of magnitude higher.

The sequence of working steps for sol-gel synthesis is not a fixed sequence. Generation of the catalysts according to the invention may be achieved, for example, by the simultaneous hydrolysis and/or condensation of Si and Ti precursors, by partial reaction of the silicon precursor compounds with corresponding amounts of water or water/catalyst and then addition of the corresponding Ti compounds or by simultaneous reaction of organic/inorganic precursor compounds with the corresponding Ti and Si compounds.

In a preferred embodiment, the organic/inorganic silicon precursor compound is initially introduced in a solvent, a catalyst and excess water, with respect to the theoretically required amount, are added and the mixture is allowed to hydrolyse, then the Ti compound is added, and the silane with free silane hydrogen units is added previously, simultaneously or later, and more water, optionally with catalyst, is added. After the formation of a gel, which may take place after from a few minutes up to a few days, depending on the composition, the catalyst, the amount of water and the temperature, the gel is immediately, or after an ageing time of up to 30 days or even longer, is dried. To fully complete the hydrolysis and condensation reactions, one or more treatments of the moist and/or already dried gel may optionally be performed using an excess of water or water vapour. Drying in air or under an inert gas preferably takes place between 50 and 250° C., in particular between 100 and 180° C.

The hydrophobicity of the organic/inorganic hybrid materials according to the invention is largely determined by the number and type of terminal and bridging Si—C bonds. These have the additional advantage, as compared with other organic bonds, such as e.g. Si—O—C bonds, that they are extremely chemically inert, i.e. they are not sensitive to hydrolysis and oxidation reactions.

The noble metals may be added in the form of precursor compounds such as salts or organic complexes or compounds during the sol-gel process, or else applied after preparation of the gel, e.g. by precipitation, impregnation in solution, incipient wetness, sputtering, as colloids or by CVD. Surface modification of the composition optionally precedes or follows this step.

Surface modification may be performed either before or after coating with the noble metal.

Modification in the context of the invention is understood in particular to be the application of groups chosen from siliconalkyl, siliconaryl, fluorine-containing alkyl or fluorine-containing aryl groups to the surface of the supported composition, wherein the groups are present in a form which is covalently or coordinately bonded to functional groups (e.g. OH groups) on the surface. However, any other surface treatment is also expressly included within the scope of the invention.

Modification may be performed either in the liquid phase or in the gas phase. In the liquid phase, modification is preferably performed at temperatures <200° C. in slightly polar or non-polar solvents, in the gas phase modification is preferably performed at temperatures <500° C. Pretreatment with liquid and/or gaseous water is advantageous in a few cases prior to modification. When compositions according to the invention are brought into contact with e.g. a silylating agent at 200° C. in the gas phase, it may be beneficial to lower the concentration of the silylating agent using a stream of an inert gas.

Modification is preferably performed with organosilicon and/or fluorine-containing organosilicon or organic compounds, wherein organosilicon compounds are preferred.

Suitable organosilicon compounds are any silylating agents known to a person skilled in the art such as organic silanes, organic silylamines, organic silylamides and their derivatives, organic silazanes, organic siloxanes and other organosilicon compounds which may obviously also be used in combination. Organosilicon compounds also expressly includes compounds of silicon and partly fluorinated or perfluorinated organic groups.

Specific examples of organic silanes are chlorotrimethylsilane, dichlorodimethylsilane, chlorobromodimethylsilane, nitrotrimethylsilane, chlorotrimethylsilane, iodo-dimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexyl-chlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxy-chlorosilane, dimethylphenylchlorosilane, methylphenylvinylchlorosilane, benzyl-dimethylchlorosilane, diphenylchlorosilane, diphenylmethylchlorosilane, diphenylvinyl-chlorosilane, tribenzylchlorosilane and 3-cyanopropyldimethylchlorosilane.

Specific examples of organic silylamines are N-trimethylsilyldiethylamine, pentafluorophenyldimethylsilylamine including N-trimethylsilylimidazoles, N-t-butyl- dimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyl-pyrrole, N-trimethylsilylpyrrolidine, N-trimethylsilylpiperidine and 1-cyanoethyl-(diethylamino)dimethylsilane.

Specific examples of organic silylamides and their derivatives are N,O-bistrimethylsilyl-acetamide, N,O-bistrimethylsilyltrifluoroacetamide, N-trimethylsilylacetaminde, N-methyl-N-trimethylsilylacetamide, N-methyl-Ntrimethylsilyltrifluoroacetamide, N-methyl-N-trimethylsilylheptafluorobutyramide, N-(t-butyldimethylsilyl)-N-fluoro-acetamide and N,O-bis(diethylhydrosilyl)trifluoroacetamide.

Specific examples of organic silazanes are hexamethyldisilazane, heptamethyldisilazane, 1,1,3,3-tetramethyldisilazane, 1,3-bis(chloromethyl)tetramethyldisilazane, 1,3-divinyl-1,1,3,3-tetramethyldisilazane and 1,3-diphenyltetramethyldisilazane.

Examples of other organosilicon compounds are N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate and N,N'-bistrimethylsilylurea.

Preferred silylating reagents are hexamethyldisilazane, hexamethyldisiloxane, N-methyl-N-(trimethylsilyl)-2,2,2-trifluoroacetramide (MSTFA) and trimethyl-chlorosilane.

Compositions according to the invention can be used at temperatures of >20° C., preferably at 80 to 240° C., particularly preferably at 120 to 215° C. The gas phase reaction is advantageously performed at elevated reaction pressures. Reaction pressures >1 bar, preferably 2 to 50 bar, are preferred. The catalyst loading is between 0.5 and 40 liters of gas per gram of catalyst and per hour.

Surprisingly, we found that compositions according to the invention which contain gold and/or silver particles and titanium-containing organic/inorganic hybrid materials, characterised in that the compositions contain Si—H groups, as compared with hitherto known catalyst systems for the catalytic oxidation of alkenes and alkanes, exhibit a catalytic activity which is higher by several orders of magnitude and long catalyst lifetimes.

Therefore, use of the supported compositions according to the invention for the oxidation of hydrocarbons is another solution to the objects mentioned above and is also another object of the invention.

The catalysts which are slightly deactivated after months can frequently be regenerated again either thermally or by washing with suitable solvents, such as e.g. alcohols, or with dilute hydrogen peroxide solutions (e.g. a 3–10% strength $H_2O_2$/methanol solution).

The composition according to the invention can basically be used for all hydrocarbons. The expression hydrocarbon is understood to cover unsaturated or saturated hydrocarbons such as olefins or alkanes, which may also contain heteroatoms such as N, O, P, S or halogens. The organic component being oxidised may be acyclic, monocyclic, bicyclic or polycyclic and may be monoolefinic, diolefinic or polyolefinic. In the case of organic components with two or more double bonds, the double bonds may be conjugated or non-conjugated. Hydrocarbons are preferably oxidised, from which oxidation products are formed which have partial pressures which are sufficiently low for the product to be constantly removed from the catalyst. Unsaturated and saturated hydrocarbons with 2 to 20, preferably 2 to 10 carbon atoms, in particular ethene, ethane, propene, propane, isobutane, isobutylene, 1-butene, 2-butene, cis-2-butene, trans-2-butene, 1,3-butadiene, pentene, pentane, 1-hexene, hexane, hexadiene, cyclohexene, benzene are preferred.

The supported compositions may be used in any physical form for oxidation reactions, e.g. milled powders, spherical particles, pellets, extrudates or granules.

A preferred use is the gas phase reaction of oxygen with hydrogen in the presence of supported compositions according to the invention. Epoxides are obtained from olefins, ketones from saturated secondary hydrocarbons and alcohols from saturated tertiary hydrocarbons in a selective manner in this way. The catalyst lifetimes extend to a few weeks, months or longer, depending on the particular reactants being used.

The relative molar ratios of hydrocarbon, oxygen, hydrogen and optionally a diluent gas can be varied over a wide range.

The molar amount of the hydrocarbon being used, with respect to the total number of moles of hydrocarbon, oxygen, hydrogen and diluent gas, may be varied over a wide range. An excess of hydrocarbon with respect to the oxygen used (on a molar basis) is preferably used. The hydrocarbon concentration is typically greater than 1 mol. % and less than 95 mol. %. Hydrocarbon concentrations in the range from 5 to 85 mol. %, in particular 10 to 80 mol. %, are preferably used.

The oxygen may be used in a wide variety of forms, e.g. molecular oxygen, air and nitrogen oxide. Molecular oxygen is preferred. The molar proportion of oxygen, with respect to the total number of moles of hydrocarbon, oxygen, hydrogen and diluent gas, may be varied over a wide range. The oxygen is preferably used in a molar deficiency with respect to the hydrocarbon. Amounts in the range 1–30 mol. %, in particular 5–25 mol. %, of oxygen are preferably used.

In the absence of hydrogen, supported compositions according to the invention exhibit only very low activity and selectivity. Up to 180° C. the productivity in the absence of hydrogen is low, at temperatures above 230° C. relatively large amounts of carbon dioxide are formed in addition to the partial oxidation products. Any known source of hydrogen may be used such as e.g. pure hydrogen, cracker hydrogen, synthesis gas or hydrogen from the dehydrogenation of hydrocarbons and alcohols. In another embodiment of the invention, hydrogen may also be produced in situ in a downstream reactor, e.g. by the dehydrogenation of propane or isobutane or alcohols such as e.g. isobutanol. The hydrogen may also be introduced into the reaction system as a complex-bonded species, e.g. a catalyst/hydrogen complex. The molar proportion of hydrogen, with respect to the total number of moles of hydrocarbon, oxygen, hydrogen and diluent gas, may be varied over a wide range. Typical hydrogen concentrations are greater than 0.1 mol. %, preferably 2–80 mol. %, in particular 5–80 mol. %.

A diluent gas such as nitrogen, helium, argon, methane, carbon dioxide, carbon monoxide or similar gases which behave in a largely inert manner may also optionally be used with the essentially required reactant gases described above. Mixtures of the inert components described may also be used. The reason for adding the inert component is to transport the heat being released by this exothermic reaction and is beneficial from a safety-engineering point of view. If the process according to the invention is performed in the gas phase, gaseous diluent components such as e.g. nitrogen, helium, argon, methane and optionally water vapour and carbon dioxide are preferably used. Although water vapour and carbon dioxide are not completely inert, they have a positive effect at very small concentrations (<2 vol. %).

If the reaction in the invention is performed in the liquid phase, an oxidation-stable and thermally stable inert liquid phase is expediently selected (e.g. alcohols, polyalcohols, polyethers, halogenated hydrocarbons, silicone oils). Supported compositions according to the invention are also suitable for the oxidation of hydrocarbons in the liquid phase. Either in the presence of organic hydroperoxides (R—OOH), olefins in the liquid phase, for instance, are highly selectively reacted to give epoxides on the catalysts described, or in the presence of hydrogen peroxide or in the presence of oxygen and hydrogen, olefins in the liquid phase are highly selectively reacted to give epoxides on the catalysts described.

We have found that the selective oxidation reaction described above has a high catalyst structure sensitivity. Given the presence of nanodisperse gold and/or silver particles in the supported composition, an advantageous increase in productivity to give the selective oxidation product was observed.

The properties of the support can advantageously be affected by incorporating oxophilic elements other than silicon, such as boron, aluminium, yttrium, tantalum, zirconium or titanium. The choice of these heteroatoms is restricted, according to the invention, to elements with redox-stable oxidation states.

The polarity of catalysts according to the invention can be sensitively adjusted, apart from the incorporation of atomic carbon, also by the incorporation according to the invention of Si—H units. The Si—H groups according to the invention and optionally present Si—C groups represent an ideal tool for adjusting the external and internal polarity for the purposes of partial oxidation.

The spatially close interplay of gold and/or silver and Ti centres on the organic/inorganic support with Si—H groups operates especially efficiently, i.e. excellent epoxidation catalysts are obtained in the presence of oxygen and hydrogen.

Compositions according to the invention can be prepared on an industrial scale without any process engineering problems and in a cost-effective manner.

The characteristic properties of the present invention are illustrated in the following examples by means of catalyst preparations and catalytic test reactions.

Obviously, it has to be understood that the invention is not restricted to the examples which follow.

EXAMPLES

Method Used to Test the Catalysts (Test Method)

A tubular metal reactor with an internal diameter of 10 mm and a length of 20 cm was used and this had been conditioned by means of an oil thermostat. The reactor was supplied with a mixture of reactant gases from four mass-flow controllers (hydrocarbon, oxygen, hydrogen, nitrogen). For reaction, 500 mg of catalyst were initially introduced at 140° C. and atmospheric pressure. The reactant gases were metered into the reactor from above. The standard catalyst loading was 3 1 of gas per (g cat.* h). Propene was chosen as an example of a "standard hydrocarbon". To perform the oxidation reactions, a stream of gas enriched with nitrogen, always called the standard gas composition in the following, was chosen: $N_2/H_2/O_2/C_3H_6=14/75/5/6\%$. The reaction gases were quantitatively analysed using gas chromatography. Gas chromatographic separation of the individual reaction products was achieved using a combined FID/TCD method in which the gases flowed through three capillary columns:

FID: HP-Innowax, 0.32 mm internal diameter, 60 long, 0.25 µm thick layer

TCD: the following columns were connected in series

HP-Plot Q, 0.32 mm internal diameter, 30 long, 20 µm thick layer

HP-Plot molecular sieve 5A, 0.32 internal diameter, 30 long, 12 µm thick layer.

Example 1

This example describes the preparation of a catalyst consisting of a silicon and titanium-containing organic/inorganic hybrid material with free silane hydrogen units which has been coated with gold particles (0.1 wt. %) using incipient wetness. With respect to silicon, the concentration of non-hydrolysable organic components was 68 mol. %, that of silane hydrogens was 31% and that of titanium was 4 mol. %.

1.9 g of a 0.1 N solution of p-toluenesulfonic acid in water were added to 10.1 g of methyltrimethoxysilane (74.1 mmol) and 15 g of ethanol (AR) and the mixture was stirred for 2 hours. Then 1.46 g of tetrabutoxytitanium (4.3 mmol) were added slowly, the mixture was stirred for a further 30 minutes, a solution of 5.6 g of triethoxysilane (34.1 mmol) was added, the mixture was again stirred for 30 minutes, a mixture of 1.23 g of a 0.1 N solution of p-toluenesulfonic acid in water was added with stirring and the mixture was then allowed to stand. The mixture reached gel-point after about 7 min. After an ageing time of 24 h, the gel was ground in a mortar and dried under air for 8 hours at 120° C.

5.4 g of sol-gel material were impregnated with a solution consisting of 540 mg of a 1% strength methanolic gold solution ($HAuCl_4 \times 3H_2O$; Merck), which had been made up to 2.8 g with methanol, the macroscopically dry material was dried for 4 h at room temperature and then conditioned for 2 h at 400° C. under a stream of nitrogen.

In a test in accordance with the test method, a constant PO selectivity of 95% was achieved. The maximum yield of PO of 8%, which was achieved after 8 h, fell back to 7.4% after 10 days.

Example 2

This example describes the preparation of a catalyst in the same way as described in example 1, but the support material is surface-modified before coating with gold.

For surface modification, 5 g of dried sol-gel material and 5 g of 1,1,1,3,3,3-hexamethyl-disilazane are initially introduced into 50 g of dry n-hexane under a protective gas and heated under reflux with stirring for 2 hours. Then the supernatant solution is decanted off, the residue is washed twice with 100 ml of n-hexane each time, volatile constituents are removed under vacuum and the product is dried for 4 hours at 150° C.

In a test in accordance with the test method, a constant PO selectivity of 95% was achieved. The maximum yield of PO of 7.5%, which was achieved after 13 h, fell back to 7.2% after 10 days.

Example 3

This example describes the preparation of a catalyst in the same way as described in example 1, but the noble metal-containing material which had been dried at room temperature was conditioned for 2 hours at 400° C. under an atmosphere of hydrogen.

In a test in accordance with the test method, a constant PO selectivity of 95% was achieved. The maximum yield of PO of 8.2%, which was achieved after 10 h, fell back to 7.6% after 10 days.

Example 4

This example describes the preparation of a catalyst consisting of a silicon and titanium-containing organic/inorganic hybrid material with free silane hydrogen units, which has been coated with gold particles (0.1 wt. %) using incipient wetness. With respect to silicon, the concentration of non-hydrolysable organic components is 94 mol. %, that of silane hydrogen is 5.5 mol. % and that of titanium is 3.9 mol. %.

1.9 g of a 0.1 N solution of p-toluenesulfonic acid solution in water were added to 10.1 g of methyltrimethoxysilane (74.1 mmol) and 15 g of ethanol (AR) and the mixture was stirred for 2 hours. Then 0.9 g of tetrapropoxytitanium (3.1 mmol) were added slowly, the mixture was stirred for another 30 minutes, a solution of 0.7 g of triethoxysilane (4.3 mmol) was added, the mixture was stirred again for 30 minutes, a mixture of 0.34 g of a 0.1 N solution of p-toluenesulfonic acid in water was added with stirring and the mixture was then allowed to stand. The mixture achieved the gel-point after about 20 h. After an ageing time of 60 h, the gel was ground in a mortar and dried for 5 hours at 120° C. under air.

2.7 g of sol-gel material were impregnated with a solution consisting of 270 mg of a 1% strength methanolic gold solution ($HAuCl_4 \times 3H_2O$; Merck), which had been made up to 1.4 g with methanol, the material was dried for 4 h at room temperature and then conditioned for 2 h at 400° C. under an atmosphere of nitrogen.

In a test in accordance with the test method, a constant PO selectivity of 95% was achieved. The maximum yield of PO of 7%, which was achieved after 12 h, fell back to 6.8% after 10 days.

Example 5

This example describes the preparation of a catalyst consisting of a silicon and titanium-containing organic/inorganic hybrid material with free silane hydrogen units, which has been coated with gold particles (0.5 wt. %) by the deposition-precipitation method. With respect to silicon, the concentration of non-hydrolysable organic components is 68 mol. %, that of silane hydrogen is 8.7 mol. % and that of titanium is 4 mol. %.

The sol-gel material was prepared in the same way as in example 1.

2 g of support were initially introduced into 15 ml of methanol (Merck, AR), 20 mg of $HAuCl_4 \times 3H_2O$ (0.1 mmol; Merck) dissolved in 5 ml of methanol were added, the pH was adjusted to 8 with 0.5 ml of 1 N $Na_2CO_3$ solution, the mixture was stirred for 30 min, 2 ml of monosodium citrate solution (32.1 g/l; pH=8) were added, the pH was checked again, the mixture was stirred for 60 min, the solids were separated, washed 3 times with 20 ml of methanol each time, dried at atmospheric pressure for 10 h at 120° C., calcined under air for 5 h at 200° C. and then conditioned under nitrogen at 400° C. for 2 h. The gold concentration in the gold/titanium/silicon catalyst was 0.48 wt. % (ICP analysis).

In a test in accordance with the test method, a constant PO selectivity of 95% was achieved. The maximum yield of PO of 4.5%, which was achieved after 5 h, fell back to 2.9% after 10 days.

Example 6

This example describes the preparation of a catalyst in the same way as described in example 1, but the catalyst support was milled before being coated with noble metal.

For milling, the titanium-containing dried material was placed in water, milled in a pearl mill ($Al_2O_3$ pearls with diameters of 0.2–0.4 mm) for 1 h at 1500 $rpm^{-1}$, the solvent was removed, the powder was dried for 4 hours at 120° C. at atmospheric pressure and then coated with 0.1 wt. % of gold as described in example 1.

In a test in accordance with the test method, a constant PO selectivity of 95% was achieved. The maximum yield of PO of 8.7%, which was achieved after 5 h, fell back to 7.9% after 10 days.

Example 7

This example describes the preparation of a catalyst in the same way as described in example 1, but the test in accordance with the test method was performed at 4 bar abs.

In a test in accordance with the test method at 4 bar abs., a constant PO selectivity of 95% was achieved. The maximum yield of PO of 10.4%, which was achieved after 7 h, fell back to 9.8% after 10 days.

Example 8

This example describes the preparation of a catalyst in the same way as described in example 1, but 60 min after adding tetrabutoxytitanium, 0.7 g of $Ta(OEt)_5$ (1.5 mmol; Chempur Co., 99.9%) was added to the homogeneous mixture, the mixture was stirred for 15 min and then triethoxysilane was added, the mixture was gelled, worked up, coated with gold and conditioned in the same way as described in example 1.

In a test in accordance with the test method, a constant PO selectivity of 95% was achieved. The maximum yield of PO of 8.1%, which was achieved after 4 h, fell back to 7.6% after 10 days.

Example 9

This example describes the preparation of a catalyst in the same way as described in example 1, but a soluble gold/cyanide precursor was used.

5.4 g of sol-gel material were impregnated with a solution consisting of 540 mg of a 1% strength methanolic gold solution ($HAuCl_4 \times 3H_2O$; Merck) and 2 mg of sodium cyanide which had been made up to 2.8 g with methanol, the material was dried for 4 h at room temperature and then conditioned for 2 h at 400° C. under an atmosphere of nitrogen.

In a test in accordance with the test method, a constant PO selectivity of 97% was achieved. The maximum yield of PO of 5%, which was achieved after 8 h, fell back to 4.9% after 10 days.

Example 10

This example describes the preparation of a catalyst in the same way as described in example 1, but polyvinylpyrrolidone had been added to the gold precursor solution.

5.4 g of sol-gel material were impregnated with a solution consisting of 540 mg of a 1% strength methanolic gold solution ($HAuCl_4 \times 3H_2O$; Merck) and 3 mg of polyvinylpyrrolidone which had been made up to 2.8 g with methanol, the material was dried for 4 h at room temperature and then conditioned for 2 h at 400° C. under an atmosphere of nitrogen.

In a test in accordance with the test method, a constant PO selectivity of 94% was achieved. The maximum yield of PO of 3.5%, which was achieved after 3 h, fell back to 2.5% after 10 days.

Example 11

This example describes the preparation of a catalyst consisting of a silicon and titanium-containing organic/inorganic hybrid material with free silane hydrogen units, which has been coated with silver particles (1 wt. %) using incipient wetness. With respect to the silicon, the concentration of non-hydrolysable organic components is 68 mol. %, that of silane hydrogen is 31.5% and that of titanium is 4 mol. %. The catalyst was prepared in the same way as described in example 1. Instead of being coated with gold particles, the catalyst support was coated with silver particles.

5.4 g of sol-gel material were impregnated with a solution consisting of 540 mg of a 10% strength aqueous silver solution ($AgNO_3$; Merck), which had been made up to 2.8 g with methanol, the material was dried for 4 h at room temperature and then conditioned for 2 h at 400° C. under an atmosphere of nitrogen.

In a test in accordance with the test method, a constant PO selectivity of 92% was achieved. The maximum yield of PO of 0.5%, which was achieved after 2 h, fell back to 0.4% after 50 hours.

Example 12

This example describes the preparation of a catalyst in the same way as described in example 11, but conditioning the silver-containing material was performed at 400° C. under an atmosphere of hydrogen.

In a test in accordance with the test method, a constant PO selectivity of 92% was achieved. The maximum yield of PO of 0.8%, which was achieved after 2 h, fell back to 0.6% after 50 hours.

Example 13

Trans-2-butene was used as an unsaturated hydrocarbon instead of propene. A catalyst analogous to the one in example 1 was used for the partial oxidation of trans-2-butene.

In a test in accordance with the test method, a constant epoxide selectivity of 94% was achieved. The maximum yield of butylene oxide of 7%, which was achieved after 6 h, fell back to 6.5% after 10 days.

Example 14

Cyclohexene was chosen as an unsaturated hydrocarbon instead of propene. A catalyst analogous to the one in example 1 was used for the partial oxidation of cyclohexene. Cyclohexene was brought into the gas phase with the aid of an evaporator.

In a test in accordance with the test method, a constant epoxide selectivity of 94% was achieved. The maximum yield of hexene oxide of 6.5%, which was achieved after 7 h, fell back to 6.3% after 10 days.

Example 15

1,3-butadiene was used as an unsaturated hydrocarbon instead of propene. A catalyst analogous to the one in example 1 was used for the partial oxidation of 1,3-butadiene.

In a test in accordance with the test method, a butene monoxide selectivity of 85% was achieved. The maximum yield of butene monoxide of 2.8%, which was achieved after 5 h, fell back to 2.3% after 10 days.

Example 16

Propane, a saturated hydrocarbon, was used instead of propene. A catalyst analogous to the one in example 1 was used for the partial oxidation of propane.

In a test in accordance with the test method, an acetone selectivity of 80% was achieved. The maximum yield of acetone of 1.5%, which was achieved after 3 h, fell back to 1.0% after 50 hours.

Example 17

Comparison Example in Accordance with EP-A1-827771

This example describes the preparation of a hydrophilic, purely inorganic catalyst support in the same way as described in EP-A1-827771, this consisting of the oxides of silicon and titanium coated with gold particles by deposition-precipitation. The Ti-containing inorganic catalyst support is obtained by impregnation of pyrogenic purely inorganic silica with titanyl acetylacetonate.

30 g of Aerosil 200 (pyrogenic silicon dioxide, Degussa, 200 m$^2$/g) were suspended in 250 ml of dry methanol, 0.98 g of titanyl acetylacetonate (3.9 mmol, Merck) were added and the mixture was stirred for 2 h at room temperature. The suspension was concentrated to dryness on a rotary evaporator, the solid was then dried at 130° C. and calcined for 3 h at 600° C. in a stream of air.

0.16 g of tetrachloroauric acid (0.4 mmol, Merck) were dissolved in 500 ml of distilled water, the pH was adjusted to 8.8 using a 2 N sodium hydroxide solution and heated to 70° C., 10 g of the titanium-containing silica described above were added and the mixture was stirred for 1 h. The solid was filtered off, washed with 30 ml of distilled water, dried for 10 h at 120° C. and calcined in air for 3 h at 400° C. According to ICP analysis, the catalyst contained 0.45 wt. % of gold.

In a test in accordance with the test method, with PO selectivities of 92%, a propene conversion of 2.3 mol. % is achieved after 20 min, a propene conversion of 1.5 mol. % is achieved after 100 min, a propene conversion of 1.0 mol. % is achieved after 4 h and a propene conversion of 0.5 mol. % is achieved after 50 h. Catalyst deactivation increased still further with increasing time.

Example 18

Comparison Example in Accordance with WO 98/00413

This example describes the preparation of a purely inorganic crystalline titanium silicalite catalyst support (TS 1) consisting of the lattice oxides of silicon and titanium which was coated with gold in the same way as described in WO 98/00413. The TS 1 catalyst support from the Leuna Co. was obtained by hydrothermal synthesis. The inorganic Si and Ti lattice silicate had an MFI structure (XRD) and it could be demonstrated, by using Raman spectroscopy, that the material did not contain any crystalline titanium dioxide phases.

10.04 g of TS 1 (Leuna) were suspended in an aqueous tetrachloroauric acid solution (0.483 g of HAuCl$_4$*3H$_2$O in 50 ml of water) in the same way as described in WO 98/00413, the pH was adjusted to 7.8 using 2 N Na$_2$CO$_3$ solution, 1.97 g of magnesium nitrate (Mg(NO$_3$)$_2$*6H$_2$O) were added, the pH was again adjusted to 7.8 using 2 N Na$_2$CO$_3$ solution and stirred for 8 h, the solid was filtered off, washed 3 times with 150 ml of H$_2$O each time, dried for 2 h at 100° C., heated to 400° C. over the course of 8 h and held at 400° C. for 5 h. The purely inorganic catalyst contained 0.95 wt. % of gold (ICP). In a test in accordance with the test method, with PO selectivities of 92%, a propene conversion of 2.5 mol. % is achieved after 20 min, a propene conversion of 1.7 mol. % is achieved after 100 min, a propene conversion of 1.6 mol. % is achieved after 4 h, a propene conversion of 1.5% is achieved after 10 h and a propene conversion of 1.1% is achieved after 100 h. Catalyst deactivation increased still further with increasing time.

Examining the Catalysts

The catalysts can advantageously be characterised by using so-called DRIFTS spectroscopy. DRIFTS (Diffuse Reflectance Infrared Fourier Transform Spectroscopy) is a well-established vibrational spectroscopic method for the structural characterisation of functional groups and adsorbates on solid surfaces. Data on the principle of the method and some application examples from the heterogeneous catalysis sector are given e.g. in the article by Mestl, G., Knözinger, H., in the Handbook of Heterogeneous Catalysis, vol. 2, p. 539 et seq. (VCH, Weinheim 1997) and in the literature cited therein.

To characterise the catalyst materials according to the invention, corresponding samples were stored for a few hours at 200° C. in a drying cabinet, transferred to an inert gas cell in the hot state and spectroscopically examined by means of DRIFTS without further contact with air (to avoid readsorption of H$_2$O at the surface of the sample).

Figure 1:
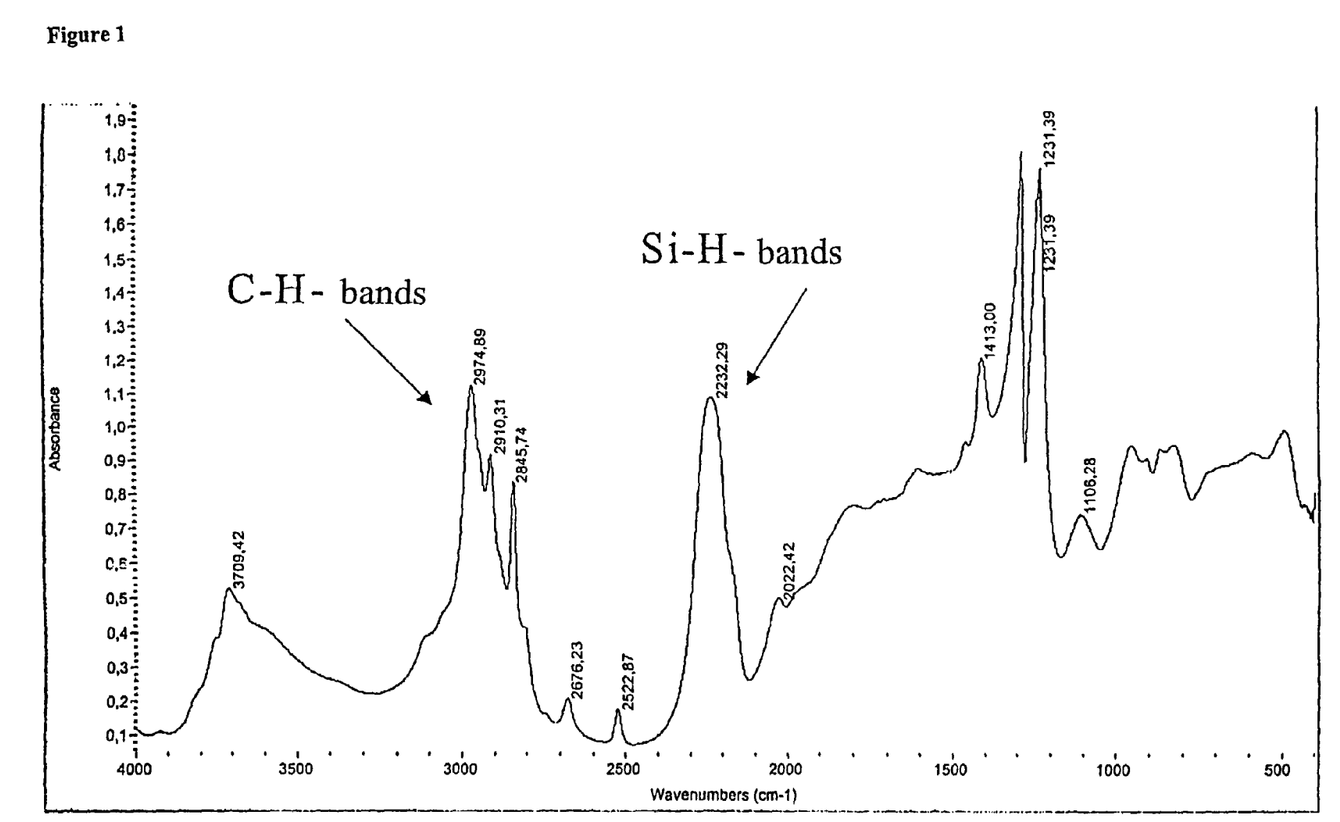
FIG. 1 illustrates the DRIFT spectrum of a noble-metal containing catalyst which is composed of the organic/inorganic hybrid material of the present invention.

FIG. 1 shows the DRIFT spectrum of a composition containing gold particles on a titanium-containing, organic/inorganic hybrid material, characterised in that the composition contains a proportion of silane hydrogens. The example shows a composition which had not been subsequently surface modified (e.g. with silylating agents).

The bands which are clearly evident at about 3000 $cm^{-1}$ in the spectrum of the composition are assigned to the hydrocarbon coating ($CH_3$ groups), those at about 2230 $cm^{-1}$ are assigned to Si—H units.

What is claimed is:

1. A composition containing gold and/or silver particles on a titanium-containing organic/inorganic hybrid material, wherein the composition contains Si—H groups, wherein the molar concentration of Si—H groups, with respect to silicon oxide content, is in the range of 0.01 to 100 mol. %.

2. The composition according to claim 1, wherein the organic/inorganic hybrid material is an organically modified glass and contains terminal and/or bridging organic groups in the network.

3. The composition according to claim 1, wherein the organic/inorganic hybrid material contains between 0.1 and 10 mol. %, with respect to silicon oxide, of titanium and optionally other foreign oxides.

4. The composition according to claim 1, wherein the composition contains between 0.001 and 4 wt. % of gold or between 0.01 and 20 wt. % of silver or a mixture thereof.

5. The composition according to claim 1, wherein the surface of the hybrid material has been modified with silicon alkyl(aryl) compounds.

6. In a process for preparing the composition according to claim 1, the improvement comprising preparing the titanium-containing organic/inorganic hybrid material with Si—H groups by a sol-gel process.

7. The process according to claim 6, wherein suitable low molecular weight compounds are mixed in a solvent and a hydrolysis and/or condensation reaction is initiated by adding water and acid or basic catalysts.

8. The process according to claim 7, wherein one or more organic acids are included as the catalyst.

9. The process according to claim 6, wherein the composition is conditioned at temperatures in the range of 100 to 1000° C. in an intermediate or final step.

10. The process according to claim 9, wherein the conditioning is performed at temperatures in the range of 200 to 600° C. under an inert gas.

11. The process according to claim 6, wherein the titanium-containing organic/inorganic hybrid material with Si—H groups is treated one or more times with a solution containing soluble gold and/or silver compounds before or after the conditioning step.

12. The process according to claim 11, wherein the solution's volume on the support is less than or equal to organic/inorganic hybrid material's pore volume.

* * * * *